United States Patent
Manian

(10) Patent No.: US 9,671,345 B2
(45) Date of Patent: Jun. 6, 2017

(54) MAPPING VOLUMES OF INTEREST IN SELECTED PLANES IN LIQUID SAMPLES

(71) Applicant: ReaMetrix, Inc., San Carlos, CA (US)

(72) Inventor: Bala S. Manian, Los Altos Hills, CA (US)

(73) Assignee: Reametrix, Inc., San Jose, CA (US)

(*) Notice: Subject to any disclaimer, the term of this patent is extended or adjusted under 35 U.S.C. 154(b) by 0 days.

(21) Appl. No.: 14/327,316

(22) Filed: Jul. 9, 2014

(65) Prior Publication Data

US 2014/0319379 A1    Oct. 30, 2014

Related U.S. Application Data

(63) Continuation-in-part of application No. 13/034,302, filed on Feb. 24, 2011.

(51) Int. Cl.
G01N 21/64 (2006.01)
G02B 21/00 (2006.01)

(52) U.S. Cl.
CPC ..... *G01N 21/6456* (2013.01); *G01N 21/6428* (2013.01); *G01N 21/6452* (2013.01); *G02B 21/0076* (2013.01)

(58) Field of Classification Search
CPC .......... G01N 21/6456; G01N 21/6428; G01N 21/6452; G02B 21/0076
USPC ........................................... 250/458.1, 459.1
See application file for complete search history.

(56) References Cited

U.S. PATENT DOCUMENTS

| | | | | | |
|---|---|---|---|---|---|
| 5,479,024 A | * | 12/1995 | Hillner | .................. | B82Y 20/00 250/458.1 |
| 5,532,873 A | * | 7/1996 | Dixon | ................ | G02B 21/0044 359/368 |
| 6,020,591 A | | 2/2000 | Harter et al. | | |
| 6,700,951 B2 | * | 3/2004 | Sumii | ................ | G01N 23/2204 378/195 |
| 2003/0151735 A1 | * | 8/2003 | Blumenfeld | ....... | G01N 21/6428 356/73 |

(Continued)

FOREIGN PATENT DOCUMENTS

WO     WO00/71991 A1    11/2000

OTHER PUBLICATIONS

Non-final Office Action mailed Aug. 8, 2014 for U.S. Appl. No. 13/034,302.

*Primary Examiner* — David Porta
*Assistant Examiner* — Gisselle Gutierrez
(74) *Attorney, Agent, or Firm* — Thomas Schneck

(57) ABSTRACT

A method and apparatus for three dimensional fluorescent analysis of a target in a liquid sample having fluorescent analyte as a target substance or fluorescent label on the target substance. A rotating carousel carries liquid samples beneath a beam having a beam spot at a horizontal plane of the sample. The carousel advances slowly a linear direction during rotation so that a pattern of overlapping spiral scans provide R-theta two-dimensional samples of the entire plane to identify locations of volumes of interest where fluorescence is measurably higher than background. These locations are probed in the depthwise direction to find locations of fluorescent analyte in three dimensions. Light from the analyte or fluorescent label is detected and processed to characterize the target by color, size or other morphology.

17 Claims, 9 Drawing Sheets

(56) References Cited

U.S. PATENT DOCUMENTS

| | | | |
|---|---|---|---|
| 2004/0113050 A1* | 6/2004 | Olszak | G02B 21/002 |
| | | | 250/208.1 |
| 2006/0256338 A1* | 11/2006 | Gratton | G01N 15/1463 |
| | | | 356/417 |
| 2011/0031420 A1* | 2/2011 | Gotz | G01F 23/292 |
| | | | 250/577 |
| 2014/0170760 A1* | 6/2014 | Tanabe | G01N 21/64 |
| | | | 436/94 |

* cited by examiner

MAPPING VOLUMES OF INTEREST IN SELECTED PLANES IN LIQUID SAMPLES

CROSS REFERENCE TO RELATED APPLICATIONS

This application is a continuation in part application of pending U.S. patent application Ser. No. 13/034,302, filed Feb. 24, 2011, which in turn claims priority from International Application No. PCT/IB2010/054965, filed on Nov. 3, 2010.

FIELD OF THE INVENTION

The invention relates generally to fluorescence measurement methods and more specifically a method to perform simultaneous measurement of bulk fluorescence emission and fluorescent event identification from liquid samples.

BACKGROUND OF THE INVENTION

Fluorescence measurements from liquid samples are useful for a variety of applications. One big area of application for such measurements is in diagnostics.

Spin processing of liquid samples for optical analysis is known. For example, in U.S. Pat. No. 6,737,238 to T. Suzuki et al. disclose a spiral path fluorescent microscope scanner for target detection at a surface. According to the '238 patent, surface scanning is performed at a rotating stage by spinning the stage while driving it linearly. A fluorescence microscope is used to detect light from a sample substrate along a path that spirals inwardly as the substrate rotates. Published application no. US 2004/0002085 to C. Shembri et al. discloses an R-theta optical scanner for biological materials on a rotating stage. Besides the R-theta format, the optical interrogation system comprises a linear stage to move the apparatus or the optics radially to view all portions of the stage.

The use of fluorescent measurements in different applications is known in the art. For example, in patent WO 0050872(A2) and WO 9909455(A1), an apparatus capable of measuring quantities of biological or other types of samples that have been labeled using any of a variety of techniques including fluorescence, radioisotopes, enzyme activated light emitting chemicals and enzyme activated fluorescent materials is provided. The provided scanner includes a source module that preferably contains an internal laser emitting two different wavelengths of approximately the same intensity. An optional external light source may be coupled to the source module, thus adding further flexibility through the addition of other wavelengths (e.g. UV, visible, mid-IR, and IR). In NL 9000622(A), the illumination system uses a coherent light source, e.g. an argon ion laser and a microscope lens assembly where the detection system which also uses the microscope lens, can detect several fluorescing colorings at various wavelengths, as well as scattered light signals. The optical focusing and tracking system uses a contactless infra-red light technique. A confocal laser-scanning microscope is used for forming an image. The invention mentioned in FR2924805 has a converter of linear polarization in radial polarization of the light beams emitted by the light source which is laid out between the light source and the interferometer thus resulting in a high resolution image. Abstract of GB 2443715 (A) describes a portable spectrophotometer suitable for harsh environments are used to identify and quantify a substance in a sample. It comprises a housing containing a light source, a probe for transmitting light from the light source to a sample to be analyzed and a probe for receiving light from the sample to be analyzed. A microprocessor comprises a reference library and an algorithm to identify a compound or class of compounds in the sample.

In case of identifying and enumerating specified blood cell subclasses, U.S. Pat. No. 4,284,412, states that a blood sample is first incubated with a reagent including antibodies to the lymphocyte subclass to be identified, the antibodies being directly or indirectly made fluorescently responsive to particular light (e.g. argon ion laser). The sample is illuminated, a cell at a time, by such focused coherent light, and forward light scatter, right angle light scatter, and fluorescence are detected and used to identify and enumerate cells of the specified subclass. WO 9508118 (A1) discloses a method and apparatus for a biological sample assay comprising forming a potentially reactive system of the sample and a fluorophore-conjugated reagent specific to a target compound, separating reacted and unreacted reagent and detecting fluorophore fluorescence in one of the separated components, the detected fluorescence being at near infrared wavelength.

WO 2006118420(A1) and US 2003133840(A1) are directed towards providing convenient and economical alternatives for detection of signals arising out of an analysis device.

An apparatus for optical testing of samples is disclosed in EP 0515129. The apparatus includes an apparatus for receiving a plurality of samples to be tested, light detection apparatus, apparatus defining light paths-extending from the plurality of samples to the light detection apparatus and apparatus for exposing the light detection apparatus to light received from individual ones of the plurality of samples along the light paths. JP 7229828 describes an invention to measure in-plane and vertical double refraction of an optical disc substrate accurately, quickly and conveniently by setting the incident plane in a plurality of directions and making an optical beam incident on the optical disc substrate. JP 2000081387(A) also describes a similar method. The invention in JP 7280741(A) detects the degree of the position shift of a true center of a wafer and a rotary center and correct the coordinates values of a foreign substance data in a surface inspecting apparatus so that at the time of observation of the foreign substance by a SEM (scanning electron microscope), a desired foreign substance can be captured easily. Similarly in JP 2001242082 (A), the sample chip containing multiple biological samples is optically scanned by means of the biological sample optical scanning device for identifying a biological sample labeled with the fluorescent material. Fluorescence from the fluorescent material excited by the light radiated from an objective lens is received by means of a light receiving member via the hollow part of a rotor to output an electric signal thus providing a biological sample optical scanning device greatly shortening an optical scanning time on a sample chip for efficient analysis and having excellent fluorescence detection sensitiveness of fluorescent material used for labeling the biological sample. DE 4307042(A1) describes the use of a laser diode which emits light in the red or near infrared wavelength region for excitation. It is possible, in combination with dye molecules whose absorption range overlaps with the laser wavelength, to reduce the background fluorescence, considerably to reduce the constructional cost, and simultaneously to use the evanescent wave when a time-saving one-step test is constructed for the optical detection of molecules, biomolecules and microorganisms.

In EP 0681178 (A1), an apparatus and method of the invention disclose a scanning imaging cytometer wherein an unprocessed biological fluid sample is reacted with a fluorescently-labeled binding agent. A spatial filter of a sufficient pinhole diameter is selected to allow simultaneous volumetric detection of all fluorescent targets in each columnar region. JP 2007020557 (A) provides an apparatus for measuring microorganisms subjected to fluorescent dyeing; wherein at a point during the measurement, if a preset numerical value is exceeded, an alarm can be given or the measurement can be suspended. WO 9835223(A1) describes a method for increasing the accuracy and the types of data measurements of laser scanned dye stained cells, in a single sample, by means of multiple assays, utilizing cell positions as a factor in merging data measurements. Change in lasers, use of different cell dye stains and different treating reagents provide additional data regarding cells of the sample and fixing of cell positions in the first assay permits merging of the data obtained in subsequent assays. Such analysis systems may be used for a single-type of analysis, however, in many practical situations, multiple analyses are required for effective identification and quantification of analytes.

EP 1219950 (A1), EP 1219951(A1) and JP 2002323437 (A) discloses a method wherein the volume of single red blood cells or other particles suspended in liquids are determined by fluorescent labeling the sample. The cell volume is determined using fluorescence intensity values measured (i) in a first area comprising a single cell, (ii) in a second area close to that cell, and (iii) in said second area, after changing the cuvette thickness by a known amount. As already noted, making parts that are well-machined having no surface irregularities are difficult, especially for those parts that are generally used once, such as sample carriers. WO 8400817(A1) mentions a method and apparatus for fluorescent immunoassay which utilizes total internal reflection at the interface between a solid phase and a liquid phase of lower index of refraction to produce an evanescent wave in the liquid phase. In WO 9702482(A1), apheresis samples are incubated with a surfactant which allows the intercalating dye to enter the WBC. A scanning instrument scans, identifies and enumerates the WBC in the apheresis sample. The system uses an adaptive intensity threshold to identify target fluorescent particles. In these cases, however, sample preparation methods and reagents may be expensive, and since liquid samples are being used, it may not be conducive for transportation and handling in a remote, scant-resource, harsh environments.

A microscale binding assay, analyte binding array, and kits are disclosed in WO 9954736(A1) which exploit the mass action law to harvest analyte from a liquid sample. This approach, coupled with direct fluorescence detection in the NIR, yields maximal signal intensity and low background for optimal sensitivity. US 2007207513 (A1) also provides methods, products and kits for identifying an analyte in a sample but the method includes combining the sample with a first reactant capable of specifically coupling to the analyte. The first reactant is then coupled to beads. The method further includes identifying the analyte in the sample by detecting the modified substrate bound to the surface of the beads and/or the reactants bound to the beads. U.S. Pat. No. 7,300,800 and U.S. Pat. No. 6,838,289 utilized a combination of fluorescent labels for labeling particles and an analyte specific fluorescent analyte detection dye. The particles contain a combination of fluorescent labels for coding the particles and an analyte specific fluorescent dye. Near infrared (NIR) fluorescent labels useful in the detection system are also provided. U.S. Pat. No. 6,905,885 describes a portable pathogen detection system that accomplishes on-site multiplex detection of targets in biological samples. The system includes: microbead specific reagents, incubation/mixing chambers, a disposable microbead capture substrate, and an optical measurement and decoding arrangement. U.S. Pat. No. 6,905,881 provides a microbead-based test plates and test methods for adjusting fluorescence imaging systems involving using a plate with fluorescent microbeads bound to a surface. U.S. Pat. No. 5,747,349 provides a method and apparatus for rapid measurement of a fluid bulk analyte, requiring only microscale volumes. Several fluid bulk analytes can be measured simultaneously and, for biological samples, the cell content can also be measured simultaneously. The invention comprises reporter beads for chemical analysis of fluid bulk properties such as pH, oxygen saturation and ion content. Despite the availability of several elegant solutions, such methods and devices are useful for single type of analysis only.

U.S. Pat. No. 5,866,433 describes an optochemical fluorescence sensor with a biorecognitive layer for measuring the concentration of one or more analytes in a sample is provided with at least one island layer which is applied on a sensor substrate. The invention in U.S. Pat. No. 5,786,219 describes novel fluorescently labeled microspheres, where the microspheres possess at least one internal fluorescent spherical zone. The invention also describes the method of preparing the novel microspheres, the method of calibrating microscopy instrumentation using the novel microspheres, the method of using the novel microspheres as distinct labels for combinatorial analysis and the use of the labeled microspheres as tagging agents and tracers. U.S. Pat. No. 5,194,300 and U.S. Pat. No. 5,132,242 describes methods of making highly fluorescent latex microsphere having a diameter of less than five hundred angstroms and has more than five thousand fluorescent markers per sphere. The microspheres are prepared by reacting an acrylic latex bead with a diamine and a fluorescent amine at elevated pH. U.S. Pat. No. 5,147,609 describes an assay element suitable for use in an automated analytical test instrument for assaying a fluid sample. The element includes a thin porous member possessing a high degree of capillarity such as a fibrous mesh pad supported within a guide defined by surfaces contiguous the porous member. U.S. Pat. No. 5,104,813 provides a dilution and mixing cartridge that allows single (or multiple) dilutions of a sample with a diluent in a disposable cartridge in which a measurement, such as optical density, is made. Addition of sample to the device automatically measures the sample, and addition of diluent automatically causes a fixed ratio of sample and diluent to enter a receiving chamber, in which mixing and measurement can take place. U.S. Pat. No. 5,053,197 describes a diagnostic assay module for analytical procedures in which an optical signal developed by interaction between a component in a sample fluid, such as an analyte in a biological fluid, and one or more reagents in a resilient assay element is read by optical means. U.S. Pat. No. 4,144,452 describes a fluorometric system to determine the kind and amount of substances derived from a biological fluid (e.g., serum or urine) or tissue in which the substances to be detected (e.g., antigen, antibody, hormone or enzyme) are coated onto a substrate surface in fluorescent form. Multiple coating areas of different samples may be employed. The fluorometric system includes a source of filtered light to excite fluorescence, an optical system for conducting the excitation light to such coating, and optical systems for receiving emitted fluorescence and for detecting the same. The invention in US 2006073611(A1) relates to methods of assaying the levels of proteins or antibodies in a test sample, and in particular, it relates to a method of determining the relative abundance of a plurality of proteins in a test sample compared to a reference. U.S. Pat. No. 7,295,316 illustrates a fluorometry device and method adapted to determine concentration of spectrally distinguishable species in a biological sample with a plurality of movable optical devices. U.S. Pat. No. 7,024,061 portrays an optical scanning device for scanning with a radiation beam a substantially circular track of an information layer. U.S. Pat. No. 6,979,830 describes methods and instrumentation for performing charge coupled device (CCD)-based confocal spectroscopy with a laser spot array are provided. The methods and instruments of the invention are useful in any spectroscopic application, including, but not limited to, microscopy and microvolume laser scanning cytometry (MLSC). In U.S. Pat. No. 6,514,770 immunoassay methods for measuring the concentration of an analyte in a test specimen are described. The methods use an immunoreagent, where one of the analyte and the immunoreagent is an antigen, and the other of the analyte and the immunoreagent is an antibody which specifically binds to the antigen. U.S. Pat. No. 4,461,973 describes a method and apparatus for measuring the concentration of a substance capable of absorbing infrared, visible or ultraviolet radiation energy, the substance being in a mixture. The method and apparatus involve passing a beam of radiant energy having predetermined spectral response characteristics through the mixture, modulating the beam at a predetermined frequency. In U.S. Pat. No. 7,102,737 a method and apparatus for detection of a particular material, such as photo-resist material, on a sample surface are disclosed. A narrow beam of light is projected onto the sample surface and the fluoresced and/or reflected light intensity at a particular wavelength band is measured by a light detector. U.S. Pat. No. 6,228,652 mentions a blood analyzing instrument includes a single transducer for simultaneously measuring the DC volume, RF conductivity, light scattering and fluorescence characteristics of blood cells passing through a cell-interrogation zone. In U.S. Pat. No. 5,939,326 a device for analyzing a whole blood sample is provided. The device comprises a conventional hematology analyzer integrated with a fluorescence cytometry analyzer. U.S. Pat. No. 5,784,152 describes a method and apparatus of analyzing samples contained in a microplate. The instrument is capable of measuring fluorescence, luminescence, and/or absorption within multiple locations within a sample well.

All of the methods and devices mentioned herein suffer from the drawbacks that include at least one of being expensive, using expensive reagents and consumable/disposable parts, not capable of being used in a harsh and resource-scant environment, and are at best capable of very limited analysis, to name a few problems. Hence, there is a dire need to make available a device that can address all these drawbacks, and accordingly a method that can be adaptable to be used in such a device.

SUMMARY OF THE INVENTION

In one aspect, the invention provides a method for measuring fluorescence emitted from a target in a liquid sample by a beam focused to a spot in a selected plane within the liquid sample. The target may be a fluorescent analyte or a tagged target emitting fluorescent radiation. The liquid sample is disposed in a spinning sample carrier beneath a fixed beam for planar R-theta scanning wherein the sample contains at least one fluorophore associated with a target substance responsive to the radiation of the incoming beam. Emitted fluorescent radiation is detected with confocal microscope detection optics so that the beam spot has a particular volume corresponding to the confocal layer spot size, at a particular depth in the sample. Those regions where the emitted fluorescent radiation exceeds a predefined threshold amount are denominated as volumes of interest, "VI". The rotating sample carrier is advanced in a linear direction so that the beam traces spiral tracks spanning the entire R-theta plane at a selected depth to map locations of VI in the plane. Other planes in the Z-direction are also scanned in the same way to confirm the statistical distribution of VI or to select another measurement plane, as well as to establish bulk background fluorescent radiation.

In another aspect, the invention provides for fluorescence measurement of rotating liquid samples with a beam probe focused to a spot in a selected R-theta plane. An incoming focused laser beam stimulates fluorescent emission from the sample, whether directly or by attachment of a fluorescent label, such as a fluorescently labeled antibody attached to a cell. The emitted light from the moving beam spot is analogous to scanning a capillary having a diameter approximately slightly larger than the beam spot diameter, i.e., the confocal depth of focus. The apparatus motion of the spot resembles, in one aspect, a flow cytometer in which the VI are distinguished from bulk emission in the scan path, while in another aspect, involving fluorescence, the bulk emission resembles a measurement from a spectrofluorometer.

The method includes acquiring simultaneous optical measurement data from the sample that is representative of one or more events in each VI as determined by data analysis. For example, different PMT detectors with different light filters can simultaneously observe the same collected light to simultaneously obtain different fluorescent spectral data. The method of data analysis comprises using the simultaneous measurement data to determine a disease condition, whether from the distribution of target substance or the bulk emission data. From the collected VI, Gaussian curve fitting can determine the intensity, size and shape of events with the VI. Such curve fitting is useful for determining the presence of cells, beads or molecules. One the other hand, the bulk emission data is useful for measuring bulk fluorescence conditions, such as glucose or cholesterol among blood cells. In this manner, spatial quantification of VI is useful in the diagnosis of disease in man, as well as for chemical analysis of fluorescent targets, whether fluorescent analytes or fluorescently tagged substances.

The method also includes doing a first low resolution scan to check centering of the sample holder on the spin axis, presence of at least some VI in the scan plane, as well as for checking various depth wise planes, with fixed R, i.e., a Z-theta scan, to find a statistically relevant plane in the Z-direction for VI, i.e., a plane having a number of VI within a mean amount. Upon identification of the proper plane, high resolution scanning maps all VI locations in the selected R-theta plane. The VI map is a table showing VI distribution in the plane.

BRIEF DESCRIPTION OF THE FIGURES

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

As used herein, sample means any substance that requires analysis for the purposes of either identification of one or more analytes, or measurement of properties, or quantification of one or more analytes, or the like, or combinations thereof. Sample may be in any given liquid form, and this includes solution, suspension, emulsion, and the like that can be penetrated by a laser beam. In some embodiments, sample is an aqueous solution, and in other embodiments, sample is a suspension in an aqueous medium. Samples are typically derived from any number of sources. In one instance, sample is derived from a body fluid. Body fluids may be derived from human or animal sources, such as primates, dogs, and the like. Body fluids include saliva, sweat, urine, sputum, mucous, semen, and the like. In another instance, sample may be derived from a fluid source, such as water from a reservoir. In yet another instance, sample may be derived from a location such as a cotton swab of a baggage at security checkpoints, which may be used as such or may be suspended in a suitable solvent for analysis.

For purposes of illustrating the invention, the samples used in describing the invention comprise at least one fluorophore. Fluorophore as used herein means any moiety that is capable of being fluorescent upon excited by a radiation corresponding to the excitation wavelength of the fluorophore, after which it emits radiation having a wavelength, which is referred to as emission wavelength. The fluorophore is attached to the remaining portion of the sample through physical linkages or through chemical linkages. Methods of incorporating fluorophores onto target materials by fluorescent tagging of target substances are well-known.

Sample is generally made available for the aforementioned purposes in a suitable sample carrier. The nature of the sample carrier depends on the nature of the sample and analysis being performed. In some instances, sample carrier is a cuvette, in other instances, sample carrier is a well, in yet other instances, sample carrier is a plate. The nature of the sample carrier will also accordingly determine the characteristics of the sample carrier. Thus, a cuvette is characterized by a wall thickness, a depth, a volume, and the like, while a well is characterized by a depth and a volume, and a plate is characterized by width and a depth. Sample may be pipetted into the sample carrier, or may be poured in, or may be added as a solid and spread along the surface through application of shear force, or prepared in situ in the sample carrier in a suitable medium, or through any other means known to those of ordinary skill in the art. Sample carriers are generally arranged in a spaced circular arrangement on a carousel that will spin under motor control.

Figure 1:
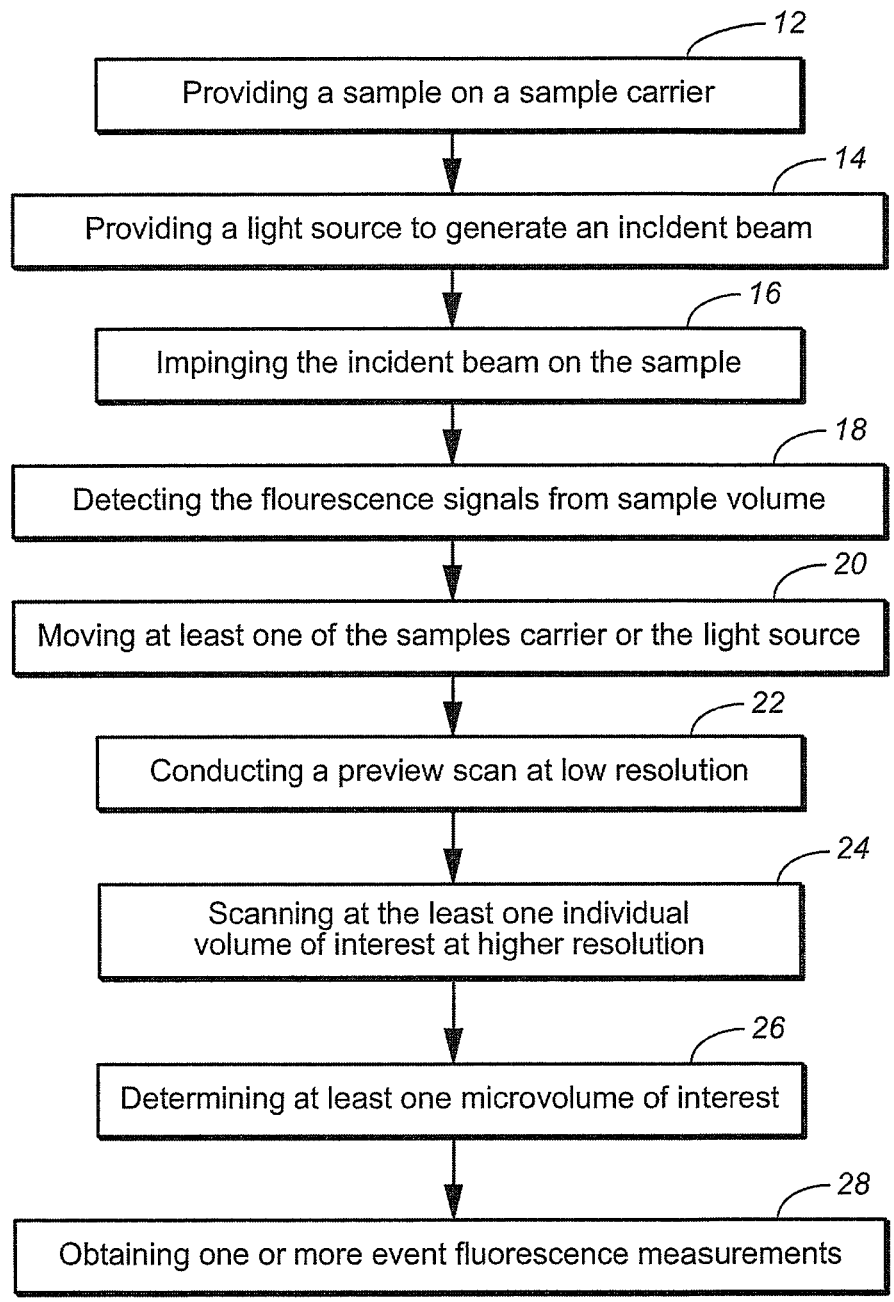
FIG. 1 is a flowchart representation of a method for measuring fluorescence according to one aspect of the invention.

As noted, in one aspect, the invention provides a method for measuring fluorescence of a sample as illustrated through flowchart 10 in FIG. 1. The method includes a step 12 for providing a sample on a sample carrier as described herein above.

The method then comprises a step 14 for providing a light source to generate an incident beam that is focused on a spot at some depth within the sample. The incident beam is typically a focused laser beam having a focal spot, called a beam probe, with wavelength, a focus diameter and a focal depth with dimensions associated with a pinhole near the detector, giving the beam probe a probe volume. The pinhole has a size and position to suppress undesired light along the optical axis, i.e. light above or below the desired focal depth. The diameter of the spot is perpendicular to the optical axis and the focal depth is in the Z-direction. Since the laser beam direction is along or parallel to the optical axis and is collimated, by moving the focusing lens in a direction along the optical axis, the probe volume can be translated along the Z-axis (optical axis) without changing characteristics of the probe volume. Wavelength of the incident beam useful in the invention ranges from about 300 nanometers (nm) to about 1200 nm. Preferred wavelengths are 488 nm and 639 nm. In one embodiment, the incident beam is a red laser beam having a wavelength of 639 nm. The implementation of a red laser source is inexpensive relative to other types of lasers. The use of a red laser source allows for the construction of a relatively inexpensive device based on the method of the invention and greater reliability of the method at ambient operating temperatures relative to other wavelengths.

As shown at step 16, the incident beam is allowed to impinge on the sample thereby causing the fluorophore portion of the sample to be excited. It may be noted that the incident beam may also sometimes be referred to as excitation beam, and the wavelength of the incident beam may be referred to as excitation wavelength. As mentioned herein the incident beam is characterized by the focus diameter, and when the incident beam impinges on the sample, the incident beam yields a laser spot that illuminates a defined volume of the sample, and described in more detail in reference to FIG. 2. The defined volume of the sample is also referred herein as a sample volume. Thus it would be appreciated by those skilled in the art that the impinging of the incident beam on the sample defines a location for the sample volume that has a defined relationship with the focus diameter of the incident beam. When the sample carrier rotates on a carousel beneath a fixed beam, the sample volume appears as a capillary where the capillary diameter is approximately equal to the sample volume diameter.

When the laser spot is focused on the sample volume, the fluorophores in the sample volume, for example fluorescent tags on target molecules, are excited giving rise to one or more fluorescence signals. The fluorescence signals pass through a pinhole that restricts the light emitted from the beam spot to a particular depth and volume. These restricted signals from the sample volume can define a volume of interest, as described below, and then simultaneously detected using a suitable detector as shown at step 18, preferably a set of 3 PMT detectors each associated with a filter of a different wavelength. In the exemplary embodiment, the choice of possible wavelengths of fluorescence signals measurable by the fluorescence detector is specifically made such that the chosen spectral region is transparent above 639 nm or at least minimally interfering to other components of the sample such as red blood cells that may otherwise severely interfere with the detection. Further, the choice of wavelengths of fluorescence signals allows the use of sample carriers that are made of plastic, which are significantly less expensive than those made of glass or other materials. For a laser at 639 nm, filters having pass bands at 655-685 nm, 705-735 nm and 750-780 nm are used. For at least at 488 nm, filters having pass bands at 510-540, 560-590, 610-640 nm are used.

The method then involves moving at least one of the sample carrier or the light source or both relative to each other to scan the sample, as shown at step 20. The movement is preferably an R-theta motion combined with linear advancement. In one embodiment, the light source is held stationary perpendicular to a sample carrier having a horizontal surface while the sample carrier is moved rotationally and linearly relative to the light source. Since the light source is stationary, a spiral scan of the sample carrier is achieved as the sample carrier is rotated in the horizontal plane, giving rise to an R-theta scan. In another embodiment, the sample carrier is moved in a reciprocating trajectory while being simultaneously moved in a linear trajectory giving rise to a faster scan, like a TV scan. The relative movement of the light source and the sample carrier is coordinated to achieve a complete scan of the R-theta or X-Y plane at a selected Z-depth. Note that the surface of the sample is not scanned because the surface is not expected to have representative VI.

Returning to FIG. 1, the method then includes a step 22 for conducting a preview scan at a low resolution in the manner as described herein. A low resolution scan has less data sampling than a high resolution scan that has much higher sampling rates. The preview scan, also sometimes referred to as an R-theta scan, is conducted at a selected Z-depth to check centering and to define at least one individual volume of interest, "VI". This scan is also used to determine a thickness of the sample carrier in the depth direction based on empirical correlation between the fluorescence signals and the focus diameter. Alternately, the focus diameter may also be pre-defined to approximately match the thickness of the sample carrier. This advantageously allows for use of the sample carrier without the necessity for prior knowledge of accurate thickness value of the sample carrier. A Z-plane is selected for measurement where VI are present in a statistically relevant manner.

When a sample comprising at least one fluorophore is present in a sample carrier, that particular region emits higher levels of fluorescence signals relative to other regions of the sample carrier, this particular region is referred herein as a volume of interest or VI. The preview scan is done to define at least one individual volume of interest within the sample volume based on the one or more fluorescence signals. The location of all volumes of interest are mapped in an R-theta plane. At the same time background characterizes bulk fluorescence of the sample selection. It is important to know the bulk measurement for diagnosis of certain conditions.

In one exemplary embodiment, for a given dimension of the sample carrier and the focus diameter, the R-theta scan is conducted in a spiral scan at a theta resolution of about 50,000 pixels per revolution and encompasses about a 2.5 mm wide scan within a 3 mm wide channel to accommodate a positional error of about 0.25 mm at about 5 micron spatial resolution at the sample plane, resulting in 500 scan lines. Preferably 50% overlap should be provided between adjacent scan lines. After detecting the one or more fluorescence signals, individual VI or volumes of interest are determined, and the VI are mapped.

The low resolution preview scan also provides a fast opportunity to check the presence of the sample carrier, to find the approximate center of the sample carrier, confirm the proper positioning of the sample in the sample carrier, confirm the absence of bubbles, proper sample loading, and other such potential problems. Thus, the preview scan can serve as a quality check on the fabrication and mounting of the sample carrier, as well as operation of the detection system.

Figure 5:
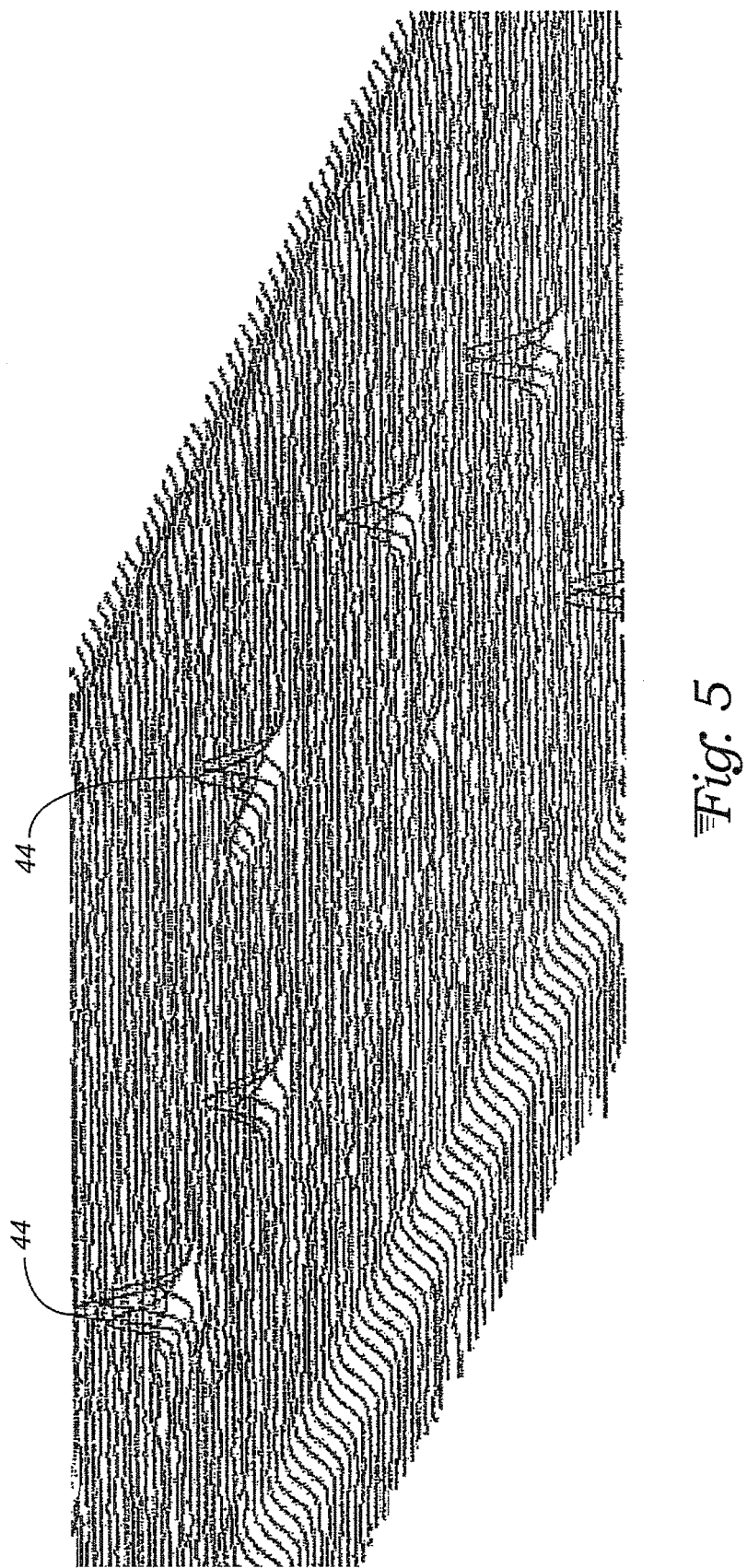
FIG. 5 is a graphical representation of fluorescence data that has been processed using a Gaussian curve-fit.

As noted herein, the R-theta scan of a depth wise plane is used to find at least one depthwise individual volume of interest where collected fluorescent light exceeds a calibrated threshold level. Other scans at low resolution of other planes are used to find a plane with relevant statistical distribution of VI. Then, the method at step 24 includes conducting a scan of the selected R-theta plane to probe the VI at higher resolution to obtain a depth profile for the fluorophores in the scan path within the sample, and also to obtain normalized bulk fluorescence measurement of the sample. Fluorophores may be distributed throughout the sample carrier. However, wherever an analyte is present, the concentration of fluorophores in that region will be greater than the remaining regions. It was observed that the optical scan of the individual volumes of interest in a sample carrier gives rise to a distribution of emitted fluorescent signals based on the presence or absence of analytes, with respect to the direction of scan. The distribution of emitted fluorescence signals is typically a Gaussian distribution. Our method involves processing the emitted fluorescence signals from the individual volumes of interest using a Gaussian curve-fitting method for each Z cross-section for a volume of interest. The processed data in the exemplary embodiment represents Gaussian-fitted intensity maximum as a function of theta, width of the Gaussian maximum (i.e. the measure of the capillary thickness), and the location of the Gaussian maximum along the Z-position, also referred to as depth profile. A optimum depth or Z-position may be useful for the next R-theta scan to obtain event fluorescence measurements. An exemplary Gaussian curve-fitted graphical data is shown in FIG. 5.

Thus, to summarize the above steps of FIG. 1, the scan at the at least one individual volume of interest at higher resolution is used to obtain a depth profile from the one or more emitted fluorescence signals of the at least one individual volume of interest. A high resolution scan has a much greater sampling point density than the low resolution scan. Further, this scan provides for a normalized bulk fluorescence measurement of the sample using the depth profile and thickness of the sample carrier.

The method then includes a step 26 for determining at least one microvolume of interest from the depth profile. As already noted herein, the region comprising the at least one fluorophore of the sample would exhibit higher intensity of one or more fluorescence signals. The microvolume of interest would typically be the region exhibiting the Gaussian maximum. Subsequently, the method includes a step 28 for extrapolating by calculating where the laser beam spot in the depth direction would be in order to obtain at least one concentrated emitted fluorescence signal from the at least one fluorophores present within the microvolume of interest. Directing a incident beam onto the sample with a focal spot size having a generally constant diameter and a depth fixed by a detector pinhole provides uniform illumination along the depth dimension of the sample carrier so that an R-theta scan can occur within the sample at a Z-level depth. This leads to a defined relationship of the spot size of the incident beam, and the depth dimension of the sample carrier so that Z-level scans at adjacent depths can be stitched together if desired to provide a three-dimensional picture of VI locations.

The method then involves a step 28 for obtaining one or more event fluorescence measurements for the sample using the at least one concentrated emitted fluorescence signal, i.e. a high resolution measurement. In one exemplary embodiment, the R-theta scan is conducted to obtain bead and cell analysis. In another example, three or more R-theta scans were performed at the appropriate microvolume of interest. It will be understood by one skilled in the art that the different scans measured herein are obtained by more than one scan. An R-theta scan or a Z-theta scan, may be conducted as the situation demands, such as when it has been determined that the whole scan sequence does not fall into one Z band. In an exemplary embodiment, the R-theta scan for a microvolume of interest can encompass about a 2 mm wide scan, resulting in 500 scan lines if the spatial resolution at the detector is 4 microns.

In the above described method, the detection of fluorescence signals is done at the different scanning steps 22, 24, 26 and 28. The method steps 22, 24, 26, and 28 of FIG. 1 also involve processing of data generated by the detection during a particular scan. In the exemplary embodiment, during an R-theta scan the data processing can include; generation of one R-theta image from a single scan or stitching together multiple Z-position level, R-theta scans, determination of the local background through pixel window spatial averaging to smooth out the effects of noise and events; subtraction of the background plus a noise floor to highlight events; using matched filter convolution to detect events; fitting a 2-D Gaussian function to characterize the events; and generating an event parameter table. At the end of any one the scanning sequences or all of the scanning sequences, an application-specific image processing software of a suitable programmable analysis device can be used to stitch or knit together all of the rotational passes over the sample to produce a final three-dimensional sample data image map showing locations of all VI.

In general, the above described method provides high-sensitivity fluorescence measurements from relatively small samples. These attributes render the method of the invention to be adapted for use when and where critical decisions are needed to be made, such as, emergency rooms, ICUs, operating rooms, and the like. The method further allows for the elimination of the need for expensive lab infrastructures, such as air conditioning and refrigeration, allowing the delivery of diagnostic information to locations beyond labs and hospitals, including resource-poor settings.

Thus the method for measuring fluorescence as described herein advantageously provides for the simultaneous detection of normalized bulk fluorescence and event fluorescence for the sample. Similarly, a device that uses the above described method would provide for rapid and accurate analysis of samples that is inexpensive in its operation and maintenance. Thus, in one embodiment, the method for measuring fluorescence as described herein is used for an assay method, and in another embodiment, the method is used for an immunoassay method. Assay methods as used herein include any in vitro testing methods and in vivo testing methods. Assay methods may also include testing of substances, for example, presence of bacteria in water. Immunoassay methods as used herein include sandwich immunoassay methods, competitive immunoassay methods, and the like. In yet another embodiment, the method for measuring fluorescence as described herein is used for cell and bead assay methods. In a further embodiment, the method of the invention is used for chemical detection, such as explosive detection, drug detection, and the like. In yet another alternate embodiment, the method for measuring fluorescence as described herein is used for flow cytometry assay. Currently, different devices are used for the different applications enumerated herein, whereas the method for measuring fluorescence as described herein provides the capability of having a single device based on the method of the invention that can be used for all of the various applications described herein.

Figure 2:
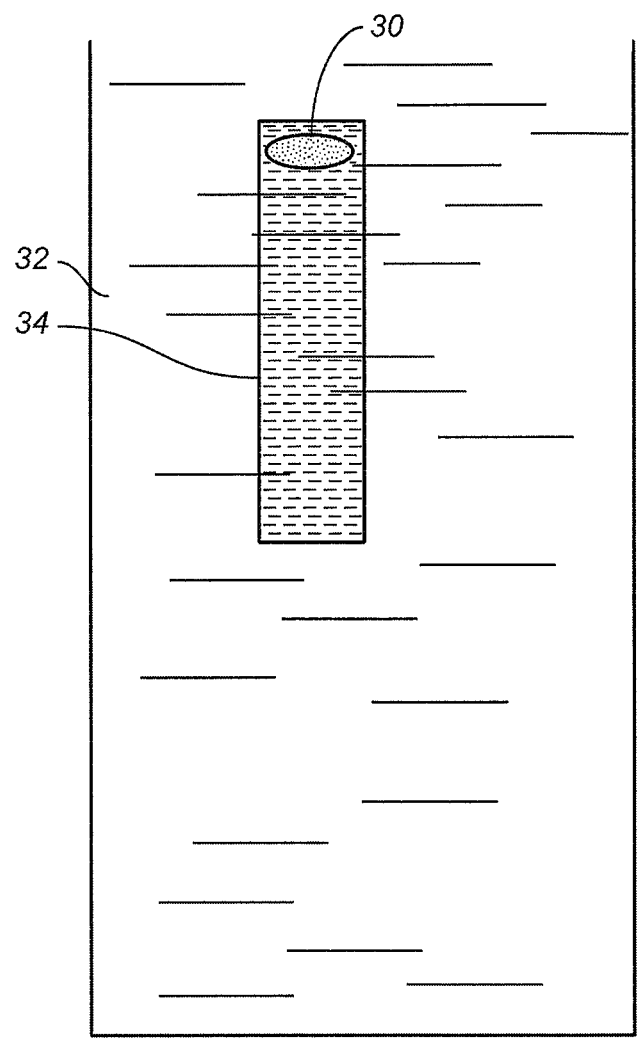
FIG. 2 is a diagrammatic representation of a laser spot and an individual volume of interest.

FIG. 2 is a diagrammatic representation of the laser spot 30 that illuminates a portion of the sample 32 that is present on a sample carrier, referred herein as a volume of interest 34 because the spot 34 has excited a nearby fluorophore and so the shaded region has higher fluorescence than surrounding regions. Note that a volume of interest will not be cylindrical as shown. The volume of interest is a geometrical region in the R-theta scan plane that intersects the sample, the exact shape of the region depends on several factors, such as, but not limited to, thickness and shape of the sample carrier, shape of the sample, refractive index of the sample medium, material making up the sample carrier, and the like.

Figure 3:
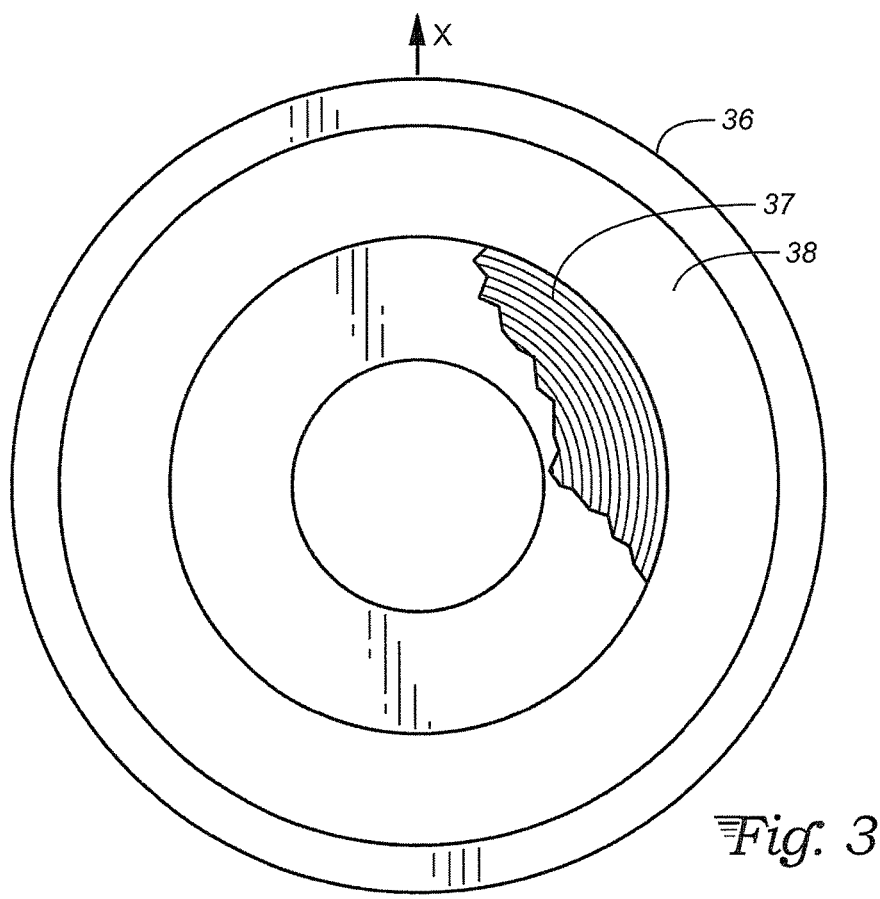
FIG. 3 is a diagrammatic representation of rotary scan obtain by moving the sample.

FIG. 3 is a diagrammatic representation of rotary scans as mentioned herein in reference to FIG. 1. As mentioned herein above, by moving the sample carrier 36 linearly in the X direction, while continuously scanning in a rotary manner, results in a series of spiral fluorescent scans 37 through the sample volume in the R-theta plane as, an annular area 38 of the sample carrier 36. Such arcuate spiral scans 37 ensure that all fluorophores of the sample are interrogated during a scanning sequence. The advantage of holding the light source and related optics part stationary during the scanning process is that the sample can be placed on rotating and translating stage while the beam spot remains perpendicular to the optical axis and the detected fluorescence is from equal size probe volumes. Further, the ability to continuously scan in a spiral orientation achieves high-precision fluorescent measurements. The moving of the sample carrier in a linear and an arcuate trajectory simultaneously can be achieved using methods known in the art. In one exemplary embodiment, the moving of the sample carrier is achieved using a stepper motor.

Figure 4:
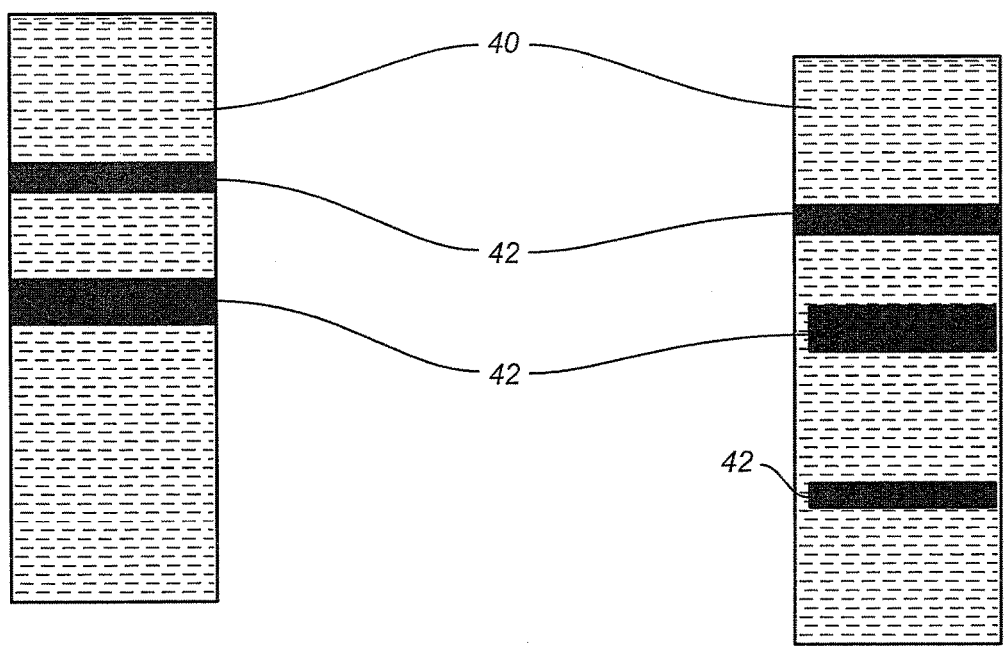
FIG. 4 is a diagrammatic representation of different microvolumes of interest within individual volumes of interest.

FIG. 4 shows a graphical representation of the sample volumes 40 and individual volumes of interest 42 as described in reference with FIG. 1. R-theta scans at different depths of the sample volume locate the volumes of interest 42. Locations of these volumes of interest are mapped as a statistical distribution of target substance in the sample.

FIG. 5 shows an exemplary Gaussian curve-fitted graphical data 44 as described in reference with FIG. 1 in order to properly locate target substance in the scan plane, as well as to determine target size.

Figure 6:
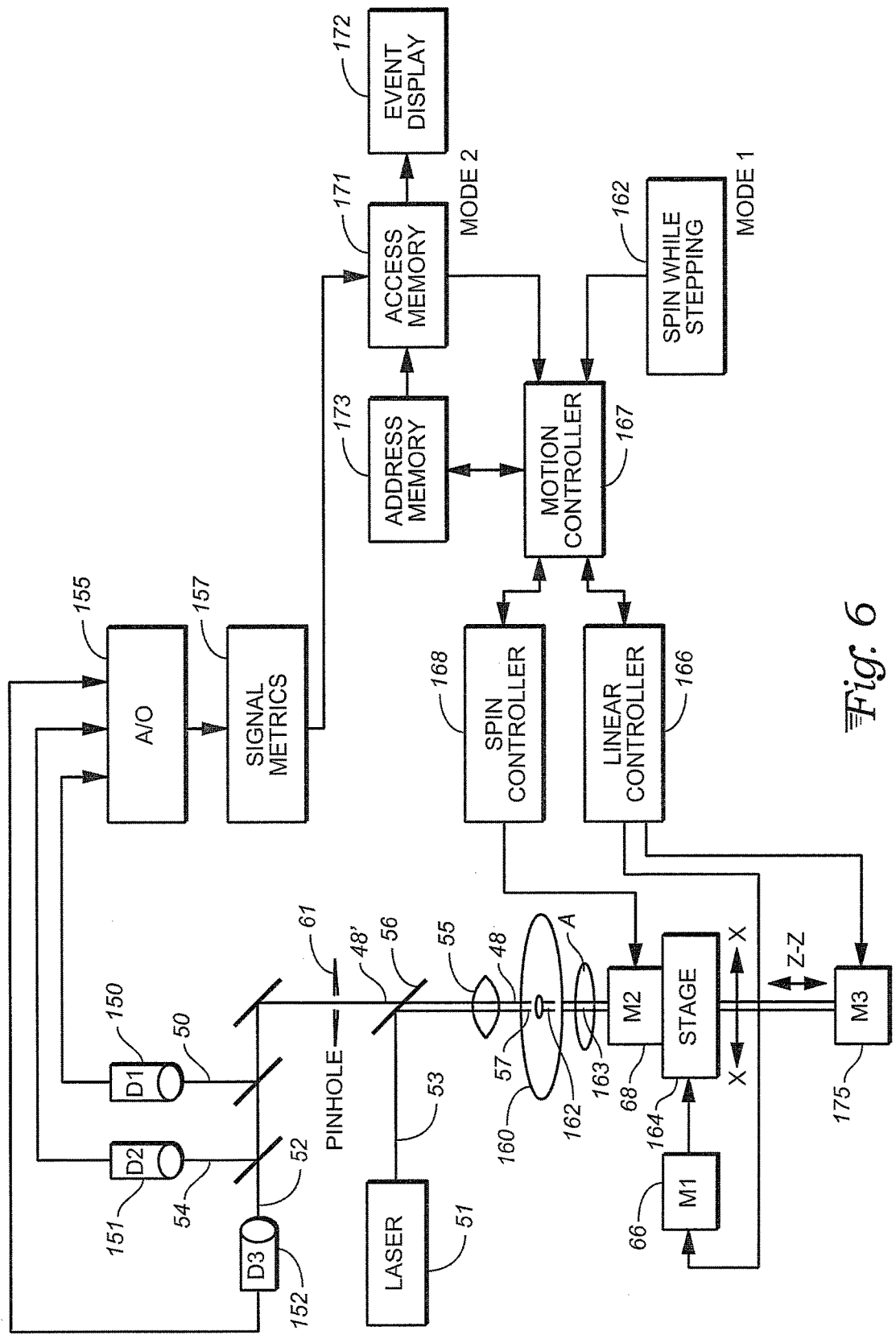
FIG. 6 shows a diagrammatic visualization of a measurement system in accordance with an embodiment of the invention.

FIG. 6 shows a diagrammatic visualization of a detection apparatus for emitted fluorescence signals as described in reference to FIG. 1. A laser 51 emits a beam 53 along an optical axis, towards the dichroic mirror 56, to be focused by lens 55 on a focal spot 57 in an R-theta scan of a sample volume that is rotating on a carousel or support 160 about a spin axis 162 for R-theta sample scans and moving in translation by stage 164 perpendicular to the optical axis. The R-theta scans are spiral scans in a manner completely scanning a surface of the sample, usually an internal depth wise slice, i.e. an internal Z-axis slice.

Stage 164, driven by linear motor 66 moves stage 164 in the x-x direction. Linear motor 66 is operated by a linear controller 166, which can be a FPGA circuit under the control of motion controller 167. The spin axis 162 of sample support 160 is rotated by stepper motor 68 as shown by arrow A to establish arcuate line scans across the sample carrier as shown in FIG. 3. Spin motor 68 is operated by a spin controller 168, a FPGA circuit under the control of motion controller 167. The motion controller 167 has two modes of operation. In a first mode, Mode 1, represented by block 162 there is a program instruction to spin in the R-theta direction while stepping in the x-x direction to form adjacent arcuate scan lines on the rotating stage with about 50% overlap of adjacent scan lines. Motion controller 167 sends the Mode 1 instruction in an appropriate format to the FPGA logic circuits of linear controller 166 and spin controller 168. A second mode of operation relates to accessing volumes of interest, VI, based upon mapped locations of the VI for Gaussian curve fitting. The R-theta scan plane can be changed in the Z direction using the vertical stepper motor 175 under the control of the linear controller 166.

The split beams 50, 54 and 52, each with a different fluorescent wavelength established by filtering the fluorescent signal beam 48' from the focal spot 57, are detected. Note that the incident beam 48 is shown as a double beam (incoming and outgoing). The outgoing beam 48' is scattered light from the sample collected by lens 55 that passes through the dichroic mirror 56. Pinhole 61 restricts light to pre-selected depth of focus in the manner of a confocal microscope, i.e., by restricting the dimensions of the signal beam 48'. Each of the split beams 50, 54, 52 impinges on a corresponding photodetector 150, 154 and 152 that transmits analog signals to a A/D converter 155 that transmits digital signals representing detected fluorescent light to signal metrics computer 157. The signal metrics computer is able to establish background fluorescence, as well as events that are statistically above background to the extent that they are defined as volumes of interest, VI. Events are mapped in a data register 171, a memory, with event data available to memory register 173.

In the second mode of operation, Mode 2, the first mode, Mode 1, is interrupted so that a VI can be explored. The data store 171 signals an event as a VI with an address in memory register 173. The motion controller 167 is commanded to direct the spin controller 168 and linear controller 166 to step to the locations in three dimensional space where the VI can be curve fit. First, the two-dimensional location of the VI in the R-theta plane is established. Next the VI are analyzed to find Gaussian curves that can characterizes the target substance. An optional data display 172 may be used to visualize events represented by VI location.

Figure 7:
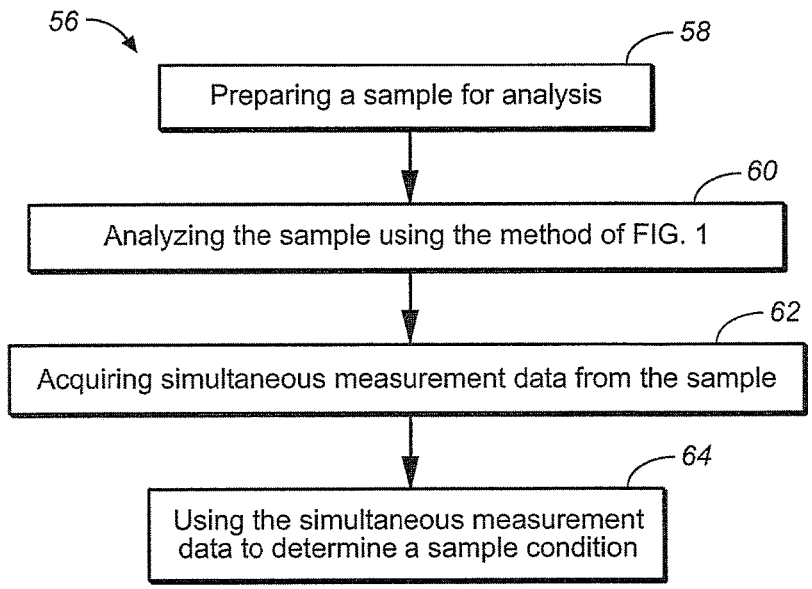
FIG. 7 is a flowchart representation of method for analyzing a sample according to aspects of the invention.

In another aspect, the invention provides a method for the analysis of a sample as represented by flowchart 56 in FIG. 7. The method of analysis comprises a step 58 for preparing a sample for analysis, wherein the sample comprises at least one fluorophore. Sample preparation may involve techniques described herein, such as, for example, adding an aliquot of blood to a reagent that comprises a fluorophore. Further, after the addition of the fluorophore, a separate step may be included to ensure adequate mixing and reaction of the reagent with blood. Exemplary techniques may include mixing, shaking, vortexing, and the like, and is known to those of ordinary skill in the art.

After preparing the sample, as indicated at step 60, it is analyzed using the method of FIG. 1 as described herein, which leads to step 62 for acquiring simultaneous measurement data from the sample. The simultaneous measurement data as used herein means any data that is representative of one or more fluorescence events for at least one individual volume of interest and the normalized bulk fluorescence for the sample. In one exemplary embodiment, the simultaneous measurement data includes the use of 3 optical detectors simultaneously observing different wavelengths for detection of the presence or absence of an antigen associated with an antibody. The antigen can be fluorescent tag. In another exemplary embodiment, the simultaneous measurement data includes the detection of presence or absence of microorganism contamination in water. In yet another exemplary embodiment, the simultaneous measurement data includes the quantification of amount of glucose present in a blood. In a further exemplary embodiment, the simultaneous measurement data includes detection of the presence or absence of a narcotic in a urine sample. Any target molecule or substance has a fluorescent tag.

As an illustration, in the case of acquiring of measurement data for the quantitation of CD-4. Sample is treated with an appropriate set of antibodies such as, MAH anti-CD4 antibody that binds to the CD-4, which is then linked to a fluorophore by mixing it with an appropriate reagent for a period of time with agitation. This is then subjected to the method of invention. Based on the intensity of the fluorescence signals arising out of the prepared sample, the amount of CD-4 cells may be quantified.

The method of analyzing a sample may further include a step 64 for using the simultaneous measurement data to determine a sample condition. In one example the sample condition may be an analyte measure within the VI. Analyte measure may include identifying the presence or absence of an analyte for example, by spectral analysis, or it may include quantification of an analyte in the sample, for example, by counting VI having analyte with particular spectra among the multiple optical detectors. The analyte measure may also be to determine a quality of a sample, such as quality of water in a region to determine if the water is potable, for example. In another example sample condition may be a disease condition. For example, the amount of CD-4 cells measured may be used to determine the susceptibility of a patient to any immunodeficiency related afflictions, and also towards making decisions towards starting treatment for such afflictions. Similarly, the simultaneous measurement data may be used to quantify the blood glucose concentration. Based on the blood glucose concentration, the determination of a disease condition, namely, diabetic or not, can be made. Blood cells can be counted in the VI, while background fluorescence can be associated with glucose. Background fluorescence associated with glucose is extracted from the general background fluorescence measurement using a calibration table for cells versus glucose background.

Further, the determination of the disease condition may be made to determine a course of a suitable treatment. This may include administration of drugs such as insulin to the patient, the dosage being determined based on several factors such as, but not limited to, medical history, medical condition, diet, weight, physical condition, and the like. The disease condition may further be classified as being one of onset, a progression, a regression, stable, and an advanced condition.

In each case, a light emitting target substance is measured relative to a background parameter.

Figure 8:
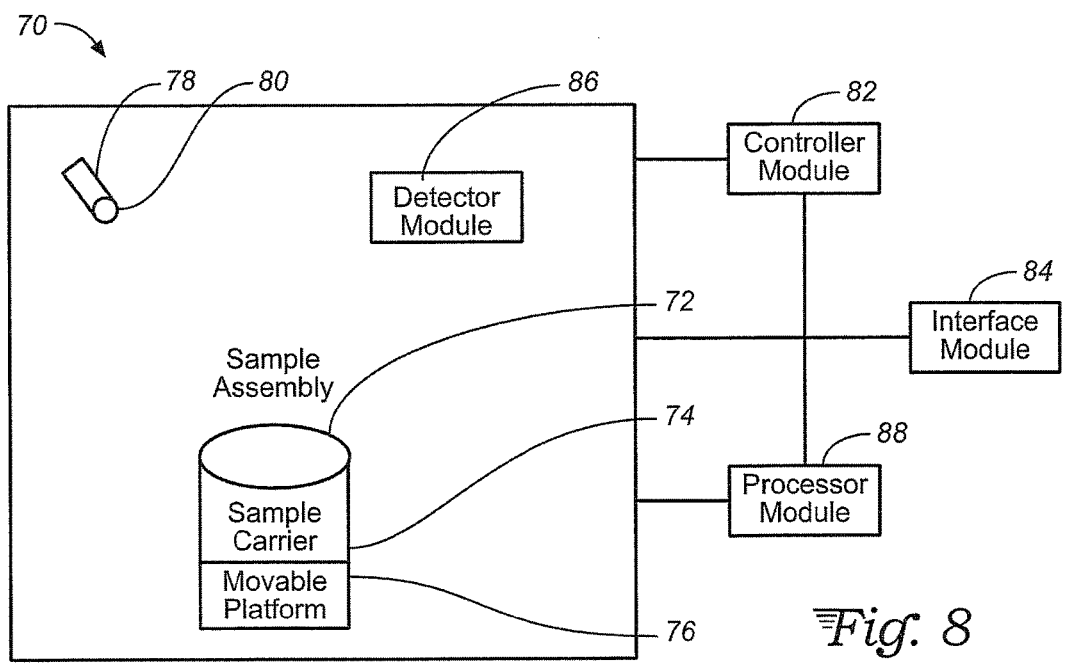
FIG. 8 is a diagrammatic representation of an exemplary embodiment of a device for measuring fluorescence according to aspects of the invention.

In yet another aspect, the invention provides a device that is based on the method for measuring fluorescence as described herein above. FIG. 8 is a simplified block diagram representation for an exemplary embodiment of the device 70 of FIG. 6. The device 70 includes a sample assembly 72 for receiving a sample carrier 74 that comprises a sample, wherein the sample comprises at least one fluorophore. The sample carrier may be any one of a channel, well, capillary, membrane, and combinations thereof. The sample carrier has a predefined region to receive the sample. Sample assembly may comprise a plurality of sample carriers, wherein all the sample carriers contain a sample or only a few sample carriers contain sample while the remaining are empty during operation of the device of the invention. In some instances, different samples may be provided in different sample carriers. Sample may be prepared in situ in the sample carrier or it may be prepared separately and then added into the sample carrier. Adding a prepared sample into the sample carrier may be achieved by known means, such as for example pipetting. The nature of the sample carrier may be specific for a particular application, i.e., in one exemplary embodiment, the sample carrier is a cuvette, and in another exemplary embodiment, the sample carrier is a capillary.

The sample assembly further includes a movable platform 76 configured in such a way that it can be attached to the sample carrier through a suitable locking means. Locking means are known to those of ordinary skill in the art, and may include fasteners, mechanical means, magnetic means, and the like. In one embodiment, the locking means is by magnetic means. In this situation, a magnetic material is present on at least part of the sample carrier, and a magnetic material of the opposite polarity and suitable magnetic strength at the complementary position of the movable platform. This will ensure that when the two components are brought together, they will be held strongly in place through magnetic attraction forces.

The movable platform in the sample assembly is further capable of being moved in a suitable trajectory. An exemplary platform is a carousel. The movement may be achieved by the use of a stepper motor. The movable platform is capable of being moved in a linear trajectory, as well as an arcuate trajectory, by spinning. In the preferred embodiment, the movable platform is moved in both a linear and an arcuate trajectory.

In FIG. 8, the device 70 includes a laser subsystem 78 that comprises a beam 80 and a dichroic beam splitter, not shown, that directs light into a focused spot or sample volume in a selected depth wise plane of the sample assembly 72. The laser provides an incident beam with a focused beam spot that impinges on the selected sample focal plane at normal incidence and the spot return signal is along the optical axis to detector module 86 through a pin hole, not shown, that establishes the focused spot in a sample volume within the selected plane. In a typical use scenario, when the movable platform moves, the entire sample assembly moves. When the incident beam is allowed to impinge on the sample, the movement of the sample assembly causes different portions of the sample to be illuminated by the incident beam, giving rise to space-dependent fluorescence signals including emitted fluorescence signals as mentioned in reference with FIGS. 1 and 6.

When the sample present on a movable platform is moved in a linear and an arcuate trajectory simultaneously, a spiral scan of the sample by the laser beam spot is achieved. The speed of rotation of the sample assembly and the linear movement are stepped by stepper motors in a coordinated manner that will vary depending on the nature of analysis being performed, and can be controlled using a controller module 82. Spiral scan lines should overlap so that an entire plane can be scanned using R-theta spiral scans. The manner in which the speeds are input to the device 70 may vary. The speeds it may be calculated by mathematical modeling with sampling rate taken into account. Thus, in one embodiment, the speeds are input through an interface module 84, while in another embodiment, the choice of a particular type of analysis from a menu in a graphical user interface module 84 will automatically select the speeds of the sample assembly. It may be understood by those skilled in the art that other displacement means replacing or in combination of the movable platform may be provided for displacing the laser spot probe volume relative to the sample volume in a three dimensional space, wherein the sample volume establishes at least one individual volume of interest. The resulting emitted fluorescence signals are detected as described herein.

As described herein above, the impinging incident beam will cause excitation of the fluorphores on the sample, giving rise to emitted fluorescence signals. These emitted fluorescence signals are then detected using detector module 86 using techniques as described in reference to the method of FIGS. 1 and 6. The detection scheme in an exemplary embodiment involves splitting the emitted and concentrated fluorescence signals into different spectral bands, where each spectral band has a specific wavelength range. Thus, a set of event fluorescences may be obtained from the sample.

The device 70 includes a processor module 88 for estimating a depth profile and a thickness of the sample carrier from the one or more emitted fluorescence signals, wherein the depth profile comprises the at least one individual volume of interest or VI. The processor module 88 is configured to use the depth profile and the thickness for measuring normalized bulk fluorescence for the sample. The processor module 88 is further configured to determine at least one microvolume of interest from the depth profile using the detected fluorescence signals and for mapping the volumes of interest. The controller module 82 is also used to trigger the light source to focus the incident beam on the microvolume of interest to obtain at least one concentrated emitted fluorescence signal. The processor module 88 may be used to measure one or more event fluorescences for the sample based on the detector signals from the microvolume of interest.

Figure 9:
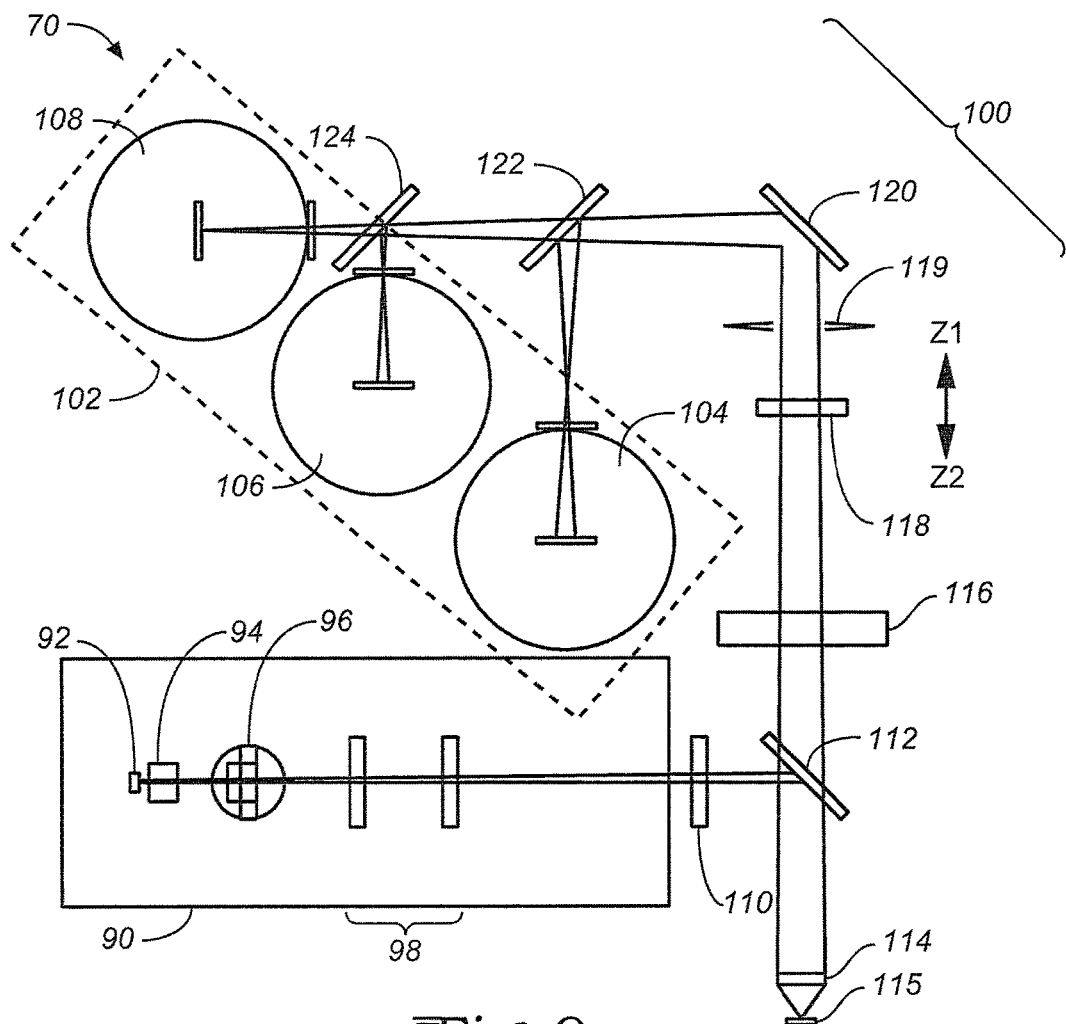
FIG. 9 is a diagrammatic representation of another exemplary embodiment of the device of FIG. 8.

FIG. 9 shows optical components of the device 70 in FIG. 8. A laser subsystem 90 includes a light source, such as a red laser diode 92 for generating an incident beam having an excitation wavelength and a focus diameter to impinge on the sample to yield a laser spot that defines a sample probe volume for measuring fluorescence. The excitation wavelength useful in the invention ranges from about 600 nm to about 800 nm. In one embodiment, the excitation wavelength is about 640 nm. The device of the invention may include, besides a red laser diode 92, a laser lens 94, a tilted glass plate 96, and a series of cylindrical lenses 98. As set forth above, the red laser diode 92 of the laser module subsystem 90 can emit a red laser beam most preferably at about 640 nm, but could be in the range from about 600 nm to about 800 nm. The emitted beam can then be directed through the laser lens 94 which collimates the light coming out of the laser diode 92. The collimated light is then directed to the tilted glass plate 96 which can act to translate the beam along the x and y axes thereby tilting the beam slightly as desired but the beam maintains normal incidence, i.e., is perpendicular to the surface of the sample, but focused inside of the sample. Scanning of the sample is achieved by rotation of the sample under the normally incident beam and not by tilting mirrors. Depth wise selection of a focal plane is achieved by adjustment of the focal lens to find a statistically relevant number of volumes of interest so that one can obtain data about the statistics of the volume of interest. Afterwards, the laser beam can be directed through the series of cylindrical lenses 98 which can expand the beam in one direction to change it from an elliptical shape (as it was emitted from the laser diode 92) to a preferred quasi-circular shape. The laser module subsystem 90 is capable of emitting an excitation laser beam which can eventually form a focused laser spot having a generally constant diameter in the sample, defining a sample probe volume that has a predefined relationship with the focus diameter.

The laser module subsystem 90 can also include a power detector (not shown). The power detector is arranged to receive a portion of the laser beam which is split off by way of, for example, the tilted glass plate 96. The power detector can monitor the power of the laser beam and feed a signal back to the laser diode 92 in order to stabilize the output of the laser diode 92 such that it emits a consistent amount of light.

The quasi-circular laser beam emitted out of the laser module subsystem 90 is then directed through the focusing and signal collection optics with scanner subsystem 100. This subsystem 100 can include a series of lenses, mirrors, filters, and the like which are arranged in a manner to direct the red laser beam onto the sample to be analyzed, and then direct the resulting emitted fluorescent signal through a pinhole 119 and then towards a series of photomultipliers (PMTs) 104, 106, 108 making up the photodetector subsystem 102 for simultaneous collection of spectral data at different wavelengths.

In this regard, the subsystem 100 can include a laser filter 110 which acts to clean up the beam that is emitted from the laser subsystem 90. The laser filter 110 cleans the beam such that only laser light is directed against the sample. The beam can then be directed against a beam splitter 112 which operates to reflect the laser beam onto the sample. The reflected laser beam is directed through a focusing lens 114 which concentrates the beam onto the sample 115 with a spot size having a generally constant diameter.

The fluorescent signal emitted from the sample 115 (including emitted and concentrated fluorescence signal described herein above) then passes through the dichroic mirror 112 and is then directed through a laser rejection filter 116. The laser rejection filter 116 acts to block any laser light from being transmitted further downstream. The emitted fluorescent signal is then directed through an adjustable focal lens 118 which operates to focus the signal on the photomultipliers (PMTs) 104, 106, 108 of the detector subsystem 102. The depth of focus of the laser spot in the sample, i.e. the probe volume, is controlled by moving focal lens 118 in the direction indicated by arrows Z1 and Z2, driven by a stepper motor, not shown. Downstream of the focal lens 118 is a pinhole 119, limiting the depth of focus of the beam spot in a confocal manner, and a folding mirror 120 which directs the signal toward two beam splitters 122, 124. The pinhole creates the sample volume that is in an imaginary capillary as the sample rotates, creating a measuring system analogous to flow cytometry. First beam splitter 122 is designed to reflect a signal in the range of about 650 nm to about 690 nm against the first PMT 104. Second beam splitter 124 is designed to reflect a signal in the range of about 690 nm to about 740 nm against the second PMT 106, while allowing a signal above about 750 nm to pass through to the third PMT 108.

Accordingly, the detector subsystem 102 can include a series of photosensitive detectors or PMTs 104, 106, 108 all of which can read in the red and near infrared region. These PMTs, along with the components of the focusing and signal collection optics 100, provide the ability to divide a fluorescent signal emitted from the sample into different spectral regions or channels. In this manner, experiments can be conducted simultaneously on a single sample through the use of a number of specific reagents for each desired experiment, thereby achieving a multiplexing capability. For example, a first reagent can be added that emits a fluorescent signal that can be divided and then read by the first PMT 104, a second reagent can be added that emits a fluorescent signal that can be divided and then read by the second PMT 106, and so on. In this manner, a single laser beam emitting at a particular wavelength (e.g. 640 nm) can be designed to excite a plurality of fluorophores, each of which then each emits at a number of different fluorescent wavelengths.

According to various embodiments, additional PMTs can be implemented into the detector subsystem 102, or stacked onto a secondary detector subsystem (not shown) which can also be arranged to read an emitted and concentrated fluorescent signal from the sample. In this manner, additional experiments could be conducted by way of the addition of additional fluorophores as well as additional laser diodes.

Such an optically-defined volume measurement facilitates the measurement of the concentration of fluorescing particles within a predefined volume (which is relatively small) and not the total fluorescence of the entire sample (a large volume). As a result, fluorescent measurements can be taken using the device 70 without needing to know the total volume of the sample being measured, since the volume over which the measurement is taken is known due to the well-defined, focused laser beam spot whose volume is specified by the beam diameter and the pinhole. The incorporation of such an optics arrangement is advantageous as it precludes the necessity of knowing the control path length of the sample assembly, thereby allowing the manufacture of cost-effective sample carriers, as well as the sample assembly in general.

Figure 10:
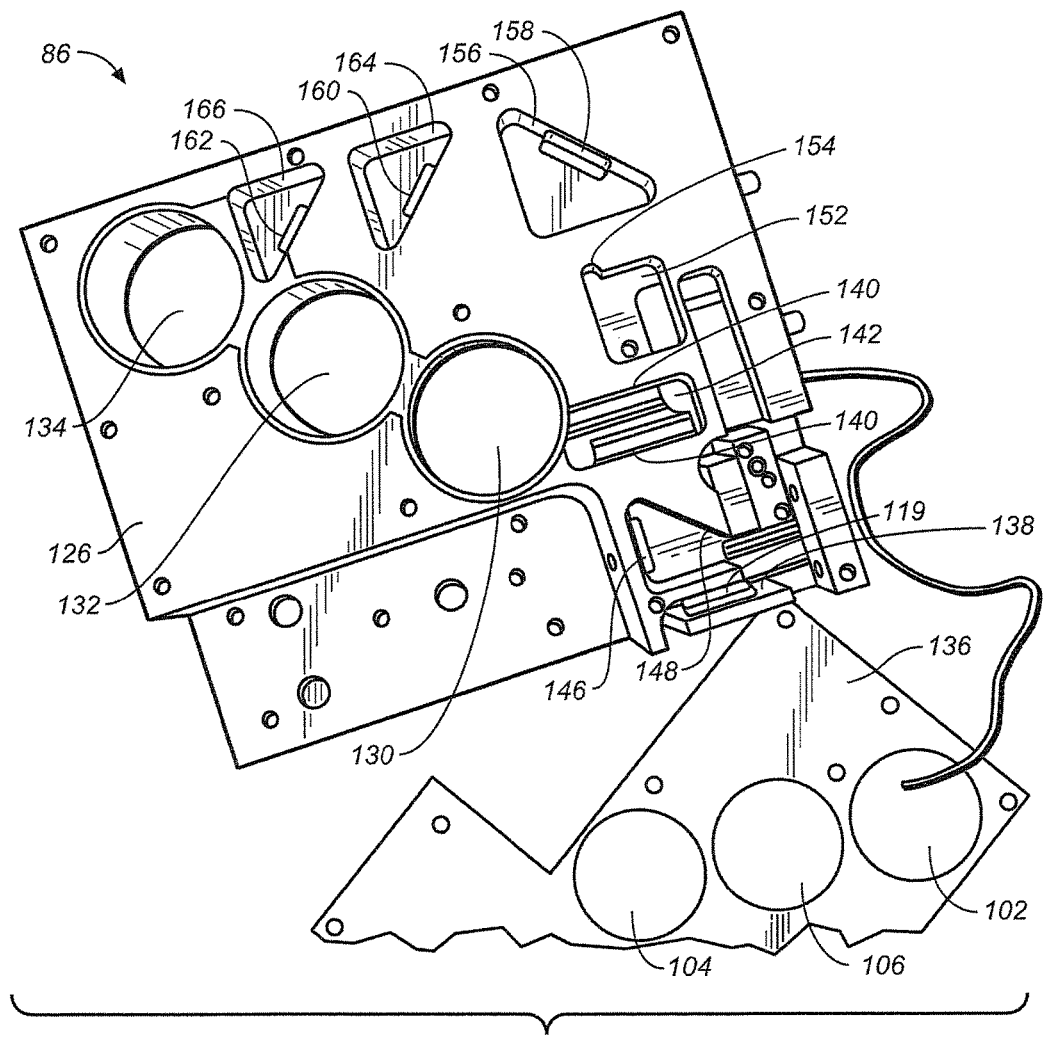
FIG. 10 is a diagrammatic representation of yet another exemplary embodiment of the device of FIG. 8.

In FIG. 10 light detection components of a stationary detector module 86 has a base plate or platform 126 with the PMTs 102, 106, 104 and a cover plate 136 removed. The PMTs 102, 106 and 104 fit into holes. The base plate 126 is formed with three holes 134, 132 and 130 into which the PMTs 102, 106, and 104 can be installed, and if necessary, more holes may be drilled into it to include more PMTs. The focusing lens 118 is shown movably secured to the base plate 126 for vertical focusing movement below pinhole 119. Laser rejection filter 140 for filtering the laser beam going into the system is shown secured vertically within a compartment 142 formed in the base plate 126.

The laser beam generated by the laser module subsystem (not shown here) can be directed through an aperture formed in the base plate 126 after which the laser beam is directed through the laser filter 146. In the same compartment, the beam splitter or folding mirror 148 can be arranged which operates to reflect the laser beam downwardly onto the focusing lens 118, as well as transmitting the emitted fluorescent signal therethrough into the next compartment 142 by way of a further aperture formed in the base plate 126. Secured to a wall of compartment 142 is the laser rejection filter 140 which only passes an entering emitted fluorescent signal while rejecting any laser light. The cleaned emitted fluorescent signal can then be directed through further apertures into a downstream compartment 152. A slot can be formed within a wall of compartment into which the focusing lens 154 is secured.

After passing through focusing lens 154 and an aperture connecting compartment 152 with compartment 156, the emitted fluorescent signal can be reflected by folding mirror 158 arranged in compartment 156 in a direction toward the first beam splitter 160 and the second beam splitter 162 through corresponding apertures in the base plate 126. The first beam splitter 160 can be secured in compartment 164 and includes apertures which allow any reflected emitted fluorescent signal to be reflected downwardly to the first PMT 104. The second beam splitter 162 can be secured in compartment 166 and can include apertures which allow any reflected emitted fluorescent signal to be reflected downwardly to the second PMT 106. An additional aperture can be provided in compartment 166 which allows any emitted fluorescent signal not reflected by either beam splitters 160, 162 to be directed toward third PMT 102.

Each of the disclosed lenses can be secured to the base plate 126 by way of an adhesive or any known way as would be appreciated in the art, such as by way of fasteners and the like.

The measurement capabilities of the device 70 of FIGS. 8 and 9, as described in different embodiments herein above, allow for the performance of diagnostic tests that have been typically done using several different instruments in a clinical diagnostic laboratory, including clinical chemistry, immunology, and cytometric assays. More particularly, the device 70 can perform various complex assays including: clinical chemistry and microbiology assays, immuno-assays (including sandwich immuno-assays and competitive immuno-assays), bead and cell enumeration assays, cytometry, cell activation and cell expression assays, and various others.

The device 70 may further be connected to a programmable analysis device, such as a laptop computer and the like. The programmable analysis device can be programmed to control the operation of the device 70, to receive sample data transmitted from the device 70, and to analyze the sample data using computerized software algorithms. For example, the programmable analysis device can be programmed to control the device such that a specific scanning sequence is performed based on the type of sample carrier to be loaded onto the device 70. The programmable analysis device can be arranged to interface with the device 70 by way of a wired and/or a wireless communication protocol.

Figure 11:
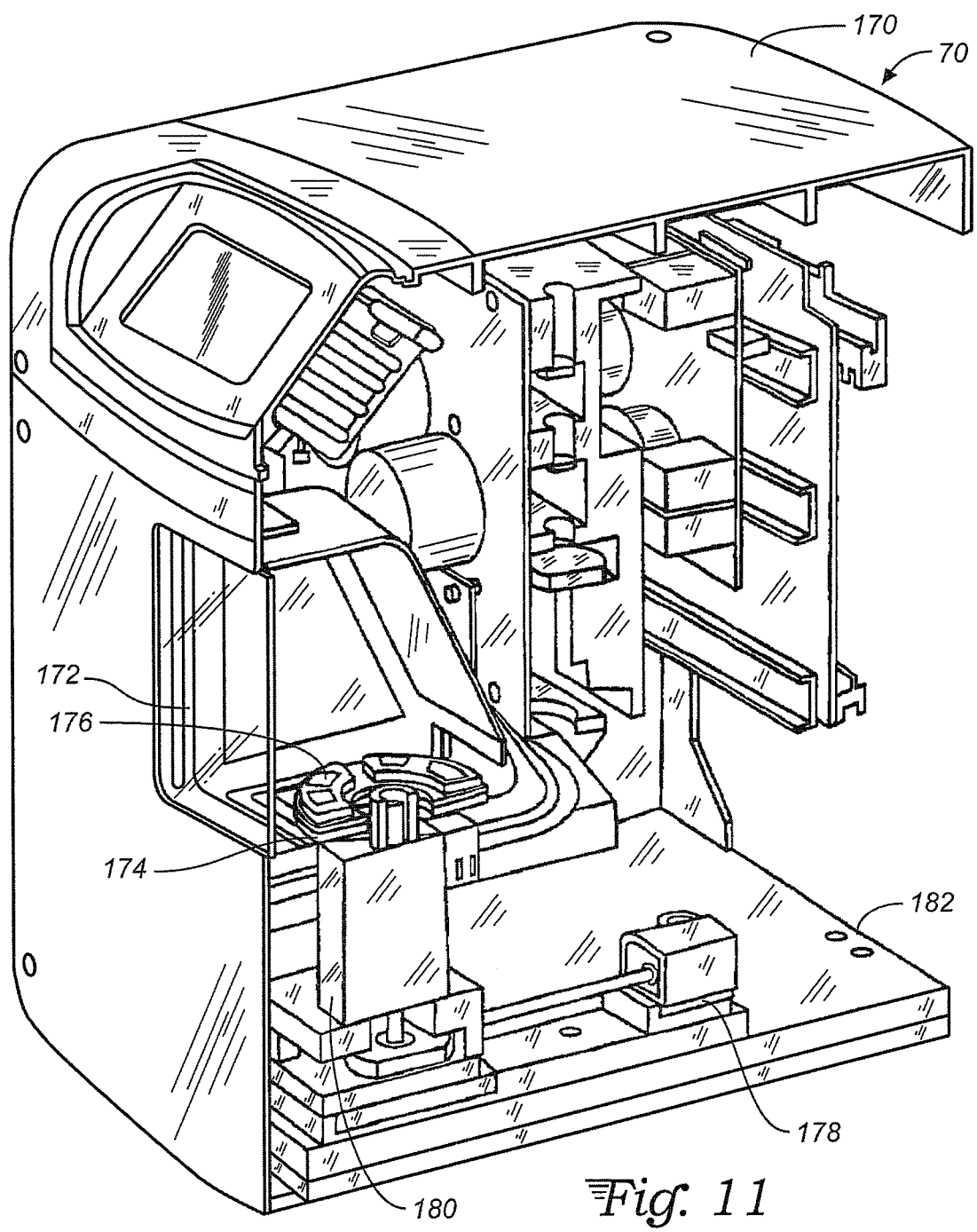
FIG. 11 is a diagrammatic representation a further exemplary embodiment of the device of the invention.

In FIG. 11 a housing for the device 70 of FIGS. 6, 8 and 9 is shown, which comprises further useful components to impart further useful capabilities to the device. The device 70 resides in a housing unit 170, wherein the device is useful as a tabletop diagnostics unit. For example, the dimensions of the housing unit 170 can be about 10 inches; wide, by about 10 inches; deep, by about 12 inches; high. The housing unit 170 can include a door 172 which can be opened and closed to allow user access to the sample assembly 174 on a rotating carousel that can be advanced by a linear stage. Access to the sample assembly 174 allows a user to insert, remove, and/or replace sample holder 176 from the device 70. The sample holder 176 may be seen to seat a sequence of wells that hold liquid sample. The movement of the sample assembly is controlled by a rotary stepper motor 178 and a linear stage stepper motor 180 to effect translation of the sample assembly in a linear trajectory and an arcuate trajectory.

The housing design obviates the need for a cooling fan that is usually necessary in such devices. This is due to the low power consumption of the device. In the exemplary implementation, the maximum power consumption was about 15 W. The device 70 can also be programmed to turn-of certain non-critical components of the device 70 during use, or while in a stand-by mode. As a result, even if the device 70 is run all day, it advantageously prevents build-up of a significant amount of heat. Notwithstanding, to dissipate any accumulation of heat, the stepper motors can be provided with cooling fins so as to reduce heat transfer to an assay application cartridges 28 as much as possible. Moreover, vents could be incorporated into the platform base 182, as well as into the top of the housing unit 170 to allow natural convection cooling of the device 70. If vents are incorporated, a filter system could also be implemented to prevent dust and other unwanted particles from entering into the interior of the detection device 70.

Once the R-theta scan is completed, locations where the fluorescent signal is higher than a predetermined level, all volumes of interest, VI, are mapped. This map is a table of VI distribution in the R-theta plane. R can be fixed and a Z-theta scan can be done to determine bulk fluorescence.

EXAMPLES

In one illustrative embodiment for the preparation of a sample for conducting a clinical chemistry measurement, a sample of whole blood is taken from a patient and at least one enzyme is added to the blood sample depending on the protein or compound being tested for. The addition of the at least one enzyme results in a reaction that produces $H_{(2)}O_{(2)}$, Alkaline Phosphate, or NAD-NADH depending on what is being tested for and whether it is present in the blood sample. The fluorophores are then added to the mixture and will create a fluorescently-tagged mixture in the presence of $H_{(2)}O_{(2)}$, Alkaline Phosphate, or NAD-NADH in the blood sample.

The device 70 as described herein is used to conduct enzyme-linked immunosorbent assay (ELISA). In conducting ELISA, a surface of an assay sample carrier is prepared, such as a plate-like surface of a channel, capillary, well, or any readable portion of the sample carrier. A known quantity of a capture antibody is then bound to this surface. Any non-specific binding sites on the prepared surface are then blocked. Afterwards, an antigen-containing blood sample is applied to the plate-like surface of the sample carrier. The plate-like surface is washed so that any unbound antigen is removed. Primary antibodies that bind specifically to the antigen in the blood sample are then applied to the sample carrier. Enzyme-linked secondary antibodies which are specific to the primary antibodies are then also applied. The plate-like surface is washed so that the unbound antibody-enzyme conjugates are removed. Substrates are then applied which are converted by the presence of an enzyme into an emitted fluorescence signal. The fluorophores are designed to fluoresce in the far red and near infrared region when excited by the red laser of the device 70.

The sample carrier can be loaded onto the sample assembly of the device 70 which conducts a rotary scan using the red laser of the device 70. Sample data is processed to create an image in the manner as discussed above. In this manner, ELISA can be conducted using the device 70.

The device 70 can be used to conduct fluorescent bead-based immuno-assays. In conducting such assays, a plurality of fluorescent beads which have been coated with a capture antibody, in addition to a secondary antibody which has been conjugated with fluorophores, can be pre-formulated, unitized, and dried within a small sample tube. The fluorophores which have been conjugated with the secondary antibody can be those, as discussed above, that are designed to fluoresce in the far red and near infrared region when excited by the red laser of the device 70.

When a user is ready to conduct an immuno-assay of a blood sample, a measured volume of the blood sample can be added to the sample tube by way of a pipette or similar device. The addition of the blood sample operates to reconstitute the formulation within the sample tube. The resulting mixture can then be incubated for a predetermined period of time, such as, for example, about 30 minutes. The incubation time is dependent on the affinity characteristics of the antibody used and the concentration of the antigen. A diluent can then be added to the sample tube and mixed for a period of time, such as, for example, several seconds.

The resulting diluted mixture in the sample tube are then delivered onto one or more micro-wells, or onto the membrane material of a sample carrier, where fluorescence measurements among a plurality of spectral channels can be conducted using the device 70. For example, fluorescence measurements can be made of (i.) the secondary antibody attached to the fluorescent beads in a first spectral channel, (ii.) the fluorescent beads in a second spectral channel, and (iii.) a reference protein having a reporter fluorescence in a third spectral channel which can act as an internal control. In this manner, fluorescent bead-based assays can be conducting using the device 70.

What is claimed is:

1. A method of rotational scanning of fluorescent light emitted from fluid samples:
   placing fluid samples in at least one sample holder in a rotating carousel that is simultaneously moved in a linear direction, the fluid samples having fluorescent light emitting target substances;
   scanning the fluid samples with low resolution R-theta scans of a beam spot with a confocal microscope arrangement detecting levels of emitted fluorescent light, including background bulk fluorescence collected by the confocal microscope arrangement at locations that define emitted fluorescent light volumes of interest exceeding background bulk fluorescence emission;
   mapping fluorescent volumes of interest of the low resolution scans in planes having fluorescent signals with specified concentrated emission; and then
   probing the planes having mapped fluorescent volumes of interest within said planes with a confocal microscope high resolution manner to establish fluorescent light emitting target substances exceeding the background bulk fluorescence emission.

2. The method of claim 1 wherein the light emitting target substances are tagged fluorescent target substances.

3. The method of claim 1 further defined by simultaneously obtaining emitted fluorescent light at different wavelengths using different detectors operating simultaneously.

4. The method of claim 1 wherein said R-theta scans are with overlapping spiral scans.

5. The method of claim 1 wherein the rotating carousel is movable in the Z-direction for Z-theta scans with fixed R for bulk fluorescence emission measurement.

6. The method of claim 1 further defined by using a laser to generate the beam spot.

7. The method of claim 1 wherein the fluid samples are placed in a plurality of sample holders spaced apart on a rotating carousel.

8. Scanning of biological samples having fluidic fluorescent target substances comprising:
   providing a rotating stage having a spin axis with liquid sample holders forming an array of fluidic fluorescent target substances on the stage;
   rotating the stage with the sample holders arranged to pass beneath a fixed beam impinging on the sample to establish an arcuate scan path, the beam capable of penetrating the liquid sample;
   incrementally advancing the stage transverse to a scan path to establish a plurality of adjacent arcuate scan paths so that a low resolution scan pattern of adjacent arcuate scan paths is formed over the rotating stage, with said rotating and incremental advancing of the rotating sample holder providing overlap of adjacent scan paths;
   mapping locations of fluorescent volumes of interest in planes having fluorescent signals representing concentrated emission, where fluorescent signals representing specified concentrated emission are returned from beam impingement near fluorescent targets during sample rotation, exceeding background fluorescent levels; and then
   probing the planes having mapped fluorescent volumes of interest within said planes in the manner of a high resolution confocal microscope for detection of fluorescent light emitting targets therein exceeding the background fluorescent levels.

9. The method of claim 8 wherein the mapped locations of fluorescent volumes of interest are analyzed with at least two detectors.

10. The method of claim 8 wherein the rotating stage is movable in the depthwise direction wherein rotation of the stage is carried out at different sample depths thereby creating three dimensional scans.

11. Scanning of biological samples having fluidic fluorescent target substances comprising:
    providing a rotating stage having a spin axis with liquid sample holders forming an array of fluidic fluorescent target substances on the stage;
    rotating the stage with the sample holders arranged to pass beneath a fixed beam impinging on the samples to establish an arcuate scan path, the beam capable of penetrating the liquid samples;
    providing confocal optics to collect light from the liquid samples at a selected depth using a plurality of detectors sensitive to light at different wavelengths characteristic of different target substances;
    incrementally advancing the stage transverse to a scan path to establish a plurality of adjacent arcuate scan paths so that a low resolution two-dimensional raster scan pattern of adjacent arcuate scan paths is formed over the rotating stage, with said rotating and incremental advancing of the rotating sample holder providing overlap of adjacent scan paths;
    mapping locations of fluorescent volumes of interest for each detector where fluorescent signals are returned from beam impingement near fluorescent targets during sample rotation, exceeding background fluorescent levels, the mapping occurring in multiple planes having fluorescent signals representing specified concentrated emission, and then
    probing the planes having mapped fluorescent volumes of interest within said planes in the manner of a high resolution confocal microscope for detection of fluorescent light emitting targets therein exceeding the background fluorescent levels.

12. The method of claim 11 further defined by using light from the detectors sensitive to light at different wavelengths to discriminate among different target substances using volumes of interest.

13. The method of claim 11 wherein the rotating stage is movable in the depthwise direction wherein rotation of the stage is carried out at different sample depths thereby creating three dimensional scans.

14. The method of claim 11 further defined by identifying target substance based upon fluorescent volumes of interest.

15. Scanning biological samples having fluidic fluorescent target substances comprising:
- establishing an array of fluidic target substances on a movable stage;
- moving the stage beneath a fixed beam impinging on the samples, the beam capable of penetrating the liquid samples;
- providing confocal optics to collect light from the liquid samples at a selected depth using a plurality of detectors sensitive to light at different wavelengths characteristic of different target substances;
- moving the stage to establish a low resolution scan pattern over the stage;
- mapping locations of fluorescent volumes of interest for each detector wherein fluorescent signals are returned from beam impingement near fluorescent targets, exceeding measured background fluorescent levels, the mapping occurring in multiple planes having fluorescent signals representing specified concentrated emission; and then
- probing the planes having mapped fluorescent volumes of interest within said planes in the manner of a high resolution confocal microscope for detection of fluorescent light emitting targets therein exceeding the background fluorescent levels.

16. The method of claim 15 further defined by using light from the detectors sensitive to light at different wavelengths to discriminate among different target substances using volumes of interest.

17. The method of claim 15 wherein the stage is movable in both the areawise direction and the depthwise direction wherein movement of the stage is carried out at different sample depths over sample areas of the two dimensional scan pattern thereby creating three dimensional scans.

* * * * *